(12) United States Patent
Kosley, Jr. et al.

(10) Patent No.: US 6,316,439 B1
(45) Date of Patent: Nov. 13, 2001

(54) GALANTHAMINE DERIVATIVES AS ACETYLCHOLINESTERASE INHIBITORS

(75) Inventors: Raymond W. Kosley, Jr., Bridgewater; Larry Davis, Sergeantsville; Veronica Taberna, Union, all of NJ (US)

(73) Assignee: Aventis Pharmaceuticals Inc., Bridgewater, NJ (US)

( * ) Notice: Subject to any disclaimer, the term of this patent is extended or adjusted under 35 U.S.C. 154(b) by 0 days.

(21) Appl. No.: 08/137,444

(22) Filed: Oct. 15, 1993

(51) Int. Cl.$^7$ .................. C07D 491/06; A61K 31/55; A61P 25/28
(52) U.S. Cl. .............................. 514/215; 540/581
(58) Field of Search .............. 540/581; 514/215

(56) References Cited

U.S. PATENT DOCUMENTS

| | | | |
|---|---|---|---|
| 4,663,318 | 5/1987 | Davis | 514/215 |
| 6,150,354 | * 11/2000 | Davis | 540/581 |

FOREIGN PATENT DOCUMENTS

| | | |
|---|---|---|
| 0236684 | 11/1987 | (EP) . |
| 0535645 | 4/1993 | (EP) . |
| 2039892 | 11/1982 | (GB) . |
| 8800350 | 9/1989 | (NL) . |
| 88-8708 | * 11/1988 | (WO) . |
| 9220327 | 5/1992 | (WO) . |

OTHER PUBLICATIONS

Han, European J. Med. Chem 27, 673 (1992).*
Nordbeng in "Alzheimer's Disease & Related Disorders" (1989), pp. 1169–1178.*
Abdalla, Phytochem. 28, 3248 (1989).*
Merck Manual, 16 Edition (1992) p. 1398.*
Liston et al, Alz. Dis. & Assoc. Disorders 2, 219 1988.*
Costa, Soc. Neuroscience Abstracts, 15, #463,10 (1989).*
Robinson, Br. J. Pharm. 98,1127 (1989).*
Sarter, Psychopharm. 107, 144 (1992).*
Thompson, N. E. J. Medicine 323, p. 445 (1990).*
Murray, et al, "Reversal By Tetrahydroaminoacridine of Scopolamine–Induced Memory and Performance Deficits in Rats" *Psychopharmacology 105*, pp.134–136 (1991).
The Merck Index, 11$^{th}$ *Edition*, 1989, pp. 9003–9004, Tacrine.
The Merck Index, 10$^{th}$ *Edition*, No. 4210, p. 620.

\* cited by examiner

*Primary Examiner*—Mark L. Berch
(74) *Attorney, Agent, or Firm*—Balaram Gupta

(57) ABSTRACT

This application relates to compounds of the formula

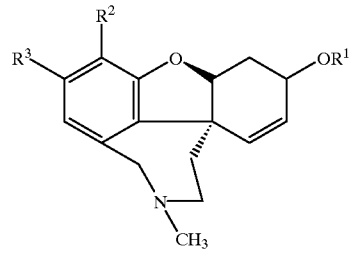

wherein $R^1$ is hydrogen, $(C_1-C_{12})$alkylcarbonyl, $(C_1-C_{12})$alkoxycarbonyl, aryl$(C_1-C_{12})$alkylaminocarbonyl, mono$(C_1-C_{18})$alkylaminocarbonyl or di$(C_1-C_8)$alkylaminocarbonyl;

$R^2$ is $(C_1-C_{12})$alkylcarbonyloxy, aryl$(C_1-C_4)$alkylcarbonyloxy, $(C_1-C_{12})$alkoxycarbonyloxy, arylcarbonyloxy, hydroxy, $(C_1-C_6)$alkoxycarbonyl $(C_1-C_6)$alkoxy or hydroxy$(C_1-C_{10})$alkoxy;

$R^3$ is hydrogen or halo; and pharmaceutically acceptable addition salts; with the proviso that when $R^2$ is hydroxy, $R^1$ and $R^3$ are not both hydrogen or when $R^2$ is hydroxy and $R^3$ is hydrogen, $R^1$ is not methylcarbonyl;

which compounds are useful for the treatment of memory dysfunction characterized by decreased cholinergic function, pharmaceutical compositions containing the compounds and methods for making and using the compounds.

49 Claims, No Drawings

GALANTHAMINE DERIVATIVES AS ACETYLCHOLINESTERASE INHIBITORS

This application relates to compounds of the formula

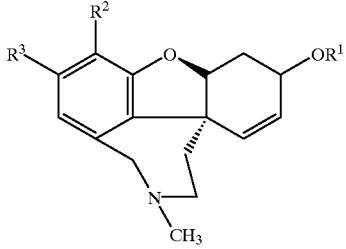

(I)

wherein $R^1$ is hydrogen, $(C_1-C_{12})$alkylcarbonyl, $(C_1-C_{12})$alkoxycarbonyl, aryl$(C_1-C_{12})$alkylaminocarbonyl, mono$(C_1-C_{18})$alkylaminocarbonyl or di$(C_1-C_8)$alkylaminocarbonyl;

$R^2$ is $(C_1-C_{12})$alkylcarbonyloxy, aryl$(C_1-C_4)$alkylcarbonyloxy, $(C_1-C_{12})$alkoxycarbonyloxy), arylcarbonyloxy, hydroxy, $(C_1-C_6)$alkoxycarbonyl $(C_1-C_6)$alkoxy or hydroxy$(C_1-C_{10})$alkoxy; and $R^3$ is hydrogen, halo or $(C_1-C_4)$alkyl; or a pharmaceutically acceptable addition salt thereof;

with the proviso that when $R^2$ is hydroxy, $R^1$ and $R^3$ are not both hydrogen;

which are useful for alleviating various memory dysfunctions characterized by decreased cholinergic function such as Alzheimer's disease.

This invention also provides a pharmaceutical composition useful for alleviating various memory dysfunctions characterized by decreased cholinergic function which comprises a compound of the invention, in an amount sufficient to affect cholinergic function and a pharmaceutically acceptable carrier. This invention further provides a method for treating the effects of Alzheimer's disease which comprises treating a patient with a pharmaceutically effective amount of a compound of the invention.

Unless otherwise stated or indicated, the following definitions shall apply throughout the specification and appended claims.

The term "alkyl" shall mean a straight or branched alkyl group of the stated number of carbon atoms. Examples include, but are not limited to methyl, ethyl, n-propyl, iso-propyl, n-butyl, isobutyl, sec-butyl, t-butyl, and straight and branched chain pentyl, hexyl, heptyl, octyl, nonyl, decyl, undecyl, dodecyl and pentadecyl.

The term "halo" shall mean chloro, fluoro, bromo and iodo.

The term "aryl" shall mean phenyl having 0, 1, 2 or 3 substituents independently selected from the group of $(C_1-C_6)$alkyl, $(C_1-C_6)$alkoxy, $(C_1-C_6)$alkylcarbonyl, halo or trifluoromethyl.

In one embodiment of the invention are compounds of the formula

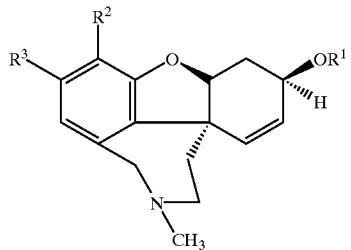

(II)

wherein $R^1$ is hydrogen, $(C_1-C_{12})$alkylcarbonyl, $(C_1-C_{12})$alkoxycarbonyl, aryl$(C_1-C_{12})$alkylaminocarbonyl, mono$(C_1-C_{18})$alkylaminocarbonyl or di$(C_1-C_8)$alkylaminocarbonyl;

$R^2$ is $(C_1-C_{12})$alkylcarbonyloxy, aryl$(C_1-C_4)$alkylcarbonyloxy, $(C_1-C_{12})$alkoxycarbonyloxy, arylcarbonyloxy, hydroxy, $(C_1-C_6)$alkoxycarbonyl $(C_1-C_6)$alkoxy or hydroxy$(C_1-C_{10})$alkoxy;

$R^3$ is hydrogen or halo; and pharmaceutically acceptable addition salts;

with the proviso that when $R^2$ is hydroxy, $R^1$ and $R^3$ are not both hydrogen.

In a preferred embodiment are compounds of Formula II wherein $R^1$ is hydrogen, $(C_1-C_{12})$alkylcarbonyl or $(C_1-C_{12})$alkoxycarbonyl; $R^2$ is $(C_1-C_{12})$ alkyl-carbonyloxy, phenylcarbonyloxy, $(C_1-C_{12})$alkoxycarbonyloxy, $(C_1-C_6)$alkoxycarbonyl$(C_1-C_6)$alkoxy or hydroxy$(C_1-C_6)$alkoxy; and $R^3$ is hydrogen or halogen.

More preferably, $R^1$ is hydrogen, $(C_1-C_8)$alkylcarbonyl or $(C_1-C_6)$alkoxycarbonyl; $R^2$ is $(C_1-C_{10})$alkylcarbonyloxy or phenylcarbonyloxy; and $R_3$ is hydrogen or bromo.

Most preferably, $R^1$ is hydrogen, methylcarbonyl, ethylcarbonyl, isopropylcarbonyl, t-butylcarbonyl or n-heptylcarbonyl; $R^2$ is methylcarbonyloxy, ethylcarbonyloxy, isopropylcarbonyloxy, t-butylcarbonyloxy, n-heptylcarbonyloxy or phenylcarbonyloxy; and $R^3$ is hydrogen or bromo.

In another type of compound of this embodiment are compounds of Formula II wherein $R^1$ is hydrogen, $(C_1-C_{12})$alkylcarbonyl or $(C_1-C_{12})$alkoxycarbonyl; $R^2$ is $(C_1-C_{12})$alkoxycarbonyloxy; and $R^3$ is hydrogen or bromo.

More preferably $R^1$ is hydrogen, $(C_1-C_{10})$alkylcarbonyl or $(C_1-C_6)$alkoxycarbonyl; $R^2$ is $(C_1-C_6)$alkoxycarbonyloxy; and $R^3$ is hydrogen or bromo.

Most preferably, $R^1$ is hydrogen, methylcarbonyl or t-butoxycarbonyl, $R^2$ is methoxycarbonyloxy, ethoxycarbonyloxy or t-butoxycarbonyloxy; and $R^3$ is hydrogen.

In yet another type of compound of this embodiment are compounds of Formula II wherein $R^1$ is hydrogen, $(C_1-C_{12})$alkylcarbonyl or $(C_1-C_{12})$alkoxycarbonyl; $R^2$ is $(C_1-C_6)$alkoxycarbonyl$(C_1-C_6)$alkoxy or hydroxy$(C_1-C_{10})$alkoxy; and $R^3$ is hydrogen or bromo.

The compounds of the invention are prepared from the appropriate optical isomer of galanthamine as described more fully below and shown in Scheme I.

SCHEME I

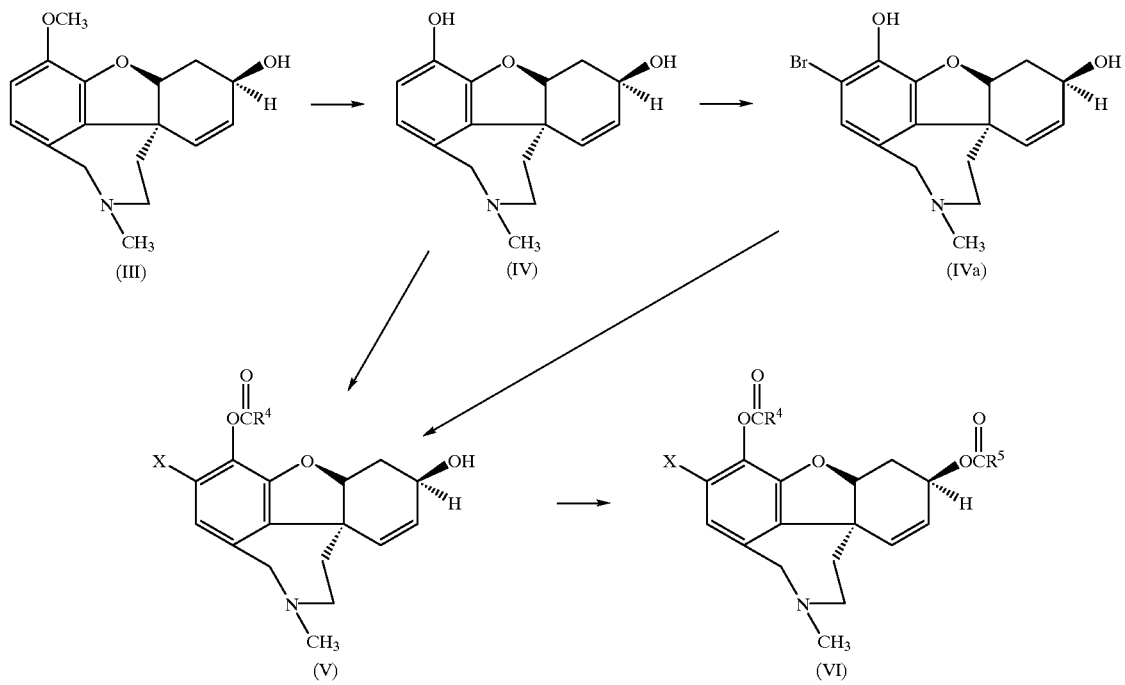

The intermediate 6-demethylgalanthamine of Formula IV, a known compound was prepared in a novel process by treating the galanthamine of Formula III an alkaline salt of ethanthiol such as, for example, with EtSLi, EtSNa or EtSK. The reaction is typically carried out in a polar nonprotic solvent such as dimethylformamide (DMF) or N-methylpyrrolidone or a protic solvent such as butanol or pentanol at from about 80° C. to about 135° C., preferably from about 90° C. to about 125° C.

The compound of Formula V where $R^4$ is alkyl or arylalkyl is prepared by reacting the compound of Formula IV or IVa with one equivalent of the appropriate anhydride in the presence of a base such as 4-dimethylaminopyridine, triethylamine or 1,8-diazabiscyclo[5.4.0]undec-7-ene. The reaction is typically carried out in a non-protic organic solvent such as, for example, chloroform or dichloromethane at from about 0° C. to about 50° C., preferably at from about 15° C. to about 30° C.

The compound of Formula V where $R^4$ is alkoxy is prepared by reacting the compound of Formula IV or IVa with the appropriate chloroformate or carbonate. The reaction is typically carried out in an inert organic solvent such as dichloromethane at from about 0° C. to about 50° C., preferably from about 15° C. to about 30° C.

In the case where $R^5$ is alkyl or aryl, the compound of Formula V is typically reacted with an appropriate carboxylic anhydride in the presence of a base such as 4-dimethylamine (DMAP) or carboxylic acid chloride in the presence of a base such as 1,8-diaza-biscyclo[5.4.0]undec-7-ene (DBU). The reactions are typically carried out in a non-protic solvent such as, for example, chloroform at from about 0° C. to about 50° C., preferably at from about 15° C. to about 30° C.

In the case where $R^5$ is alkoxy, the compound is reacted with the appropriate chloroformate in the presence of an amine such as triethylamine; or with the appropriate carbonate in the presence of an amine such as DMAP. The reactions are typically carried out in an inert organic solvent such as methylene chloride at from about −10° C. to about 50° C., preferably from about 0° C. to about 30° C.

The compound of Formula VI can be prepared from the compound of Formula V. In the case where $R^6$ is alkylamino or arylamino, a solution of the appropriate isocyanate and the compound V in a nonprotic solvent such as tetrahydrofuran in a sealed tube at from about 55° C. to about 85° C. for from about 24 hours to about 120 hours, preferably from about 60° C. to about 70° C. for from about 60 hours to about 80 hours. Alternatively, where $NR^4R^5$ and $R^8$ are identical, the compounds are made from the compound of Formula IV using over two moles of the appropriate isocyanate in a sealed tube as described above.

In the case where X is Br, the compound of Formula IV is treated with bromine in the presence of an amine such as t-butylamine to obtain the brominated compound. The bromine is first added to the t-butylamine at from about −20° C. to about −30° C., the mixture is then cooled to about −70° C. to about −78° C. and the galanthamine compound is then added and the mixture allowed to warm to room temperature over 6 to 10 hours, preferably about 8 hours. The reaction is typically carried out in a nonpolar organic solvent such as for example toluene at from about −80° C. to about room temperature for from about 6 hours to about 10 hours, preferably about 8 hours.

The compounds of Formula I of the present invention can be used for the treatment of various memory dysfunctions characterized by decreased cholinergic function, such as Alzheimer's disease. The compounds of the present invention are advantageous because they are less toxic and more specific to brain acetylcholinesterase than the related compounds known in the art. In addition, the 6-O-demethyl ester and carbonate derivatives of this invention can cleave to yield 6-O-demethylgalanthamine, a known acetylcholinesterase inhibitor.

This utility is manifested by the ability of these compounds to inhibit the enzyme acetylcholinesterase and thereby increase acetylcholine levels in the brain.

The ability to inhibit acetylcholinesterase was determined by the photometric method of Ellman et al., Biochem. Pharmacol. 7,88 (1961). Results of acetylcholinesterase inhibition for some of the compounds of this invention are presented in Table I along with those for reference compounds.

TABLE I

Acetylcholinesterase Inhibition Assay

| Compound | $IC_{50}$ $\mu M$ CHE I |
|---|---|
| 6-O-Demethyl-6-O-(trimethylacetyl)galanthamine hydrochloride | 2.688 |
| 6-O-Demethyl-6-O-(2-propoxycarbonyl)galanthamine | 1.612 |
| Tacrine | 0.32 |

This utility can also be ascertained by determining the ability of these compounds to restore cholinergically deficient memory in the Dark Avoidance Assay. In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compounds, resulting in a greater interval before re-entry into the dark compartment.

The test results are expressed as the percent of a group of animals in which the effect of scopolamine is blocked, as manifested by an increased interval between being placed in the test chamber and reentering the dark compartment. Results of Dark Avoidance Assay for some of the compounds of this invention are presented in Table II along with a result for a reference compounds.

TABLE II

| Compound | SDDA Dose (mg/kg, s.c.) | Percent of Animals with Scopolamine Induced Memory Deficit Reversal |
|---|---|---|
| 6-O-Demethyl-6-O-(trimethylacetyl)-galanthamine | 0.10 | 53 |
| 6-O-Demethyl-6-O-(2-propoxy carbonyl)galanthamine hydrochloride | 0.10 | 33 |
| 6-O-Demethyl-3-O-(2-propoxy-carbonyl)-6-O-(t-butylcarbonyl)-galanthamine hydrochloride hydrate | 0.10 | 53 |
| Tacrine | 0.31 | 33 |

Effective quantities of the compounds of the invention may be administered to a patient by any of the various methods, for example, orally as in capsule or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartaric, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compounds, but may be varied depending upon the particular form and may conveniently be between 5% to about 70% of the weight of the unit. The amount of active compound in such compositions is such that a suitable dosage will be obtained. Preferred compositions and preparations according to the present invention are prepared so that an oral dosage unit form contains between 1.0–200 milligrams of active compound.

The tablets, pills, capsules, troches and the like may also contain the following ingredients: a binder such as microcrystalline cellulose, gum tragacanth or gelatin: an excipient such as starch or lactose, a disintegrating agent such as alginic acid, Primogel, cornstarch and the like; a lubricant such as magnesium stearate or Sterotex; a glidant such as colloidal silicon dioxide; and a sweeting agent such as sucrose or saccharin may be added or a flavoring agent such as peppermint, methyl salicylate, or orange flavoring. When the dosage unit form is a capsule, it may contain, in addition to materials of the above-type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes, colorings and flavors. Materials used in preparing these various compositions should be pharmaceutically pure and non-toxic in the amounts used.

For the purpose of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present inventions are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents, such as benzyl alcohol or methyl parabens; antioxidants such as ascorbic acid or sodium bisulfite; chelating agents such as ethylenediaminetetraacetic acid; buffers such as acetates; citrates or phosphates and agents for the adjustment of tonicity such as sodium chloride or dextrose. The parenteral multiple dose vials may be of glass or plastic.

The following Table III and examples will further illustrate this invention but are not intended to limit it in any way. In Table III typical compounds of the instant invention are listed. The melting points are for hydrochloride salts unless otherwise indicated. Following Table m, representative illustrative preparations of compounds of the invention are described.

solution was added a solution of 0.57 g of galanthamine in 5.7 ml of dry DMF. The solution was stirred at 95–100° for 2 hours and subsequently at 100–105° for 3 hours, allowed to cool to room temperature and concentrated to an oil. The

TABLE III

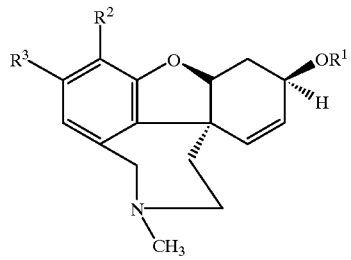

| EX. No. | $R^1$ | $R^2$ | $R^3$ | m.p. ° C. |
|---|---|---|---|---|
| 1 | H | OH | H | 225–229[a] |
| 2 | C(=O)CH(CH$_3$)$_2$ | OC(=O)CH(CH$_3$)$_2$ | H | 200 |
| 3 | H | OC(=O)C(CH$_3$)$_3$ | H | 250–251 |
| 4 | C(=O)CH$_2$CH$_3$ | OC(=O)CH$_2$CH$_3$ | H | 170–171 |
| 5 | H | OC(=O)CH$_3$ | H | 244–246 |
| 6 | C(=O)CH$_3$ | OC(=O)CH$_3$ | H | 142 |
| 7 | C(=O)CH$_3$ | OH | H | 162d |
| 8 | C(=O)C(CH$_3$)$_3$ | OC(=O)C(CH$_3$)$_3$ | H | 265 |
| 9 | H | OC(=O)OCH(CH$_3$)$_2$ | H | 218 |
| 10 | C(=O)CH(CH$_3$)$_2$ | OC(=O)C(CH$_3$)$_3$ | H | 248 |
| 11 | H | OC(=O)C$_6$H$_5$ | H | 144–145[a] |
| 12 | C(=O)(CH$_2$)$_6$CH$_3$ | OC(=O)C(CH$_3$)$_3$ | H | 185–187 |
| 13 | C(=O)(CH$_2$)$_6$CH$_3$ | OC(=O)CH$_2$CH$_3$ | H | 215d |
| 14 | C(=O)OC(CH$_3$)$_3$ | OC(=O)OC(CH$_3$)$_3$ | H | 154d |
| 15 | H | OH | Br | 138–141 |
| 16 | H | OC(=O)C(CH$_3$)$_3$ | Br | 275–278 |
| 17 | H | OC(=O)CH$_2$CH$_3$ | H | 221–223 |
| 18 | H | OC(=O)CH$_3$ | Br | 236–288 |
| 19 | H | OC(=O)OCH$_3$ | H | 195d |
| 20 | H | OC(=O)OCH$_2$CH$_3$ | H | 208d |
| 21 | H | OC(=O)OC(CH$_3$)$_3$ | H | 237d |
| 22 | H | OC(=O)(CH$_2$)$_6$CH$_3$ | H | 158–161 |
| 23 | H | OC(=O)(CH$_2$)$_3$CH$_3$ | H | 208–210 |
| 24 | H | OC(=O)(CH$_2$)$_4$CH$_3$ | H | 212–215 |
| 25 | H | OC(=O)(CH$_2$)$_5$CH$_3$ | H | 178–180 |
| 26 | C(=O)OC(CH$_3$)$_2$CH$_2$CH$_3$ | OC(=O)CH$_3$ | H | 178–180d |
| 27 | C(=O)OC(CH$_3$)$_2$CH$_2$CH$_3$ | H | H | 175d |
| 28 | C(=O)OC(CH$_3$)$_2$CH$_2$CH$_3$ | OCH$_3$ | H | 167d |
| 29 | H | OCH$_2$C(=O)OCH$_2$CH$_3$ | H | oil |
| 30 | H | OC(=O)OC(CH$_3$)$_2$CH$_2$CH$_3$ | H | 129–130 |
| 31 | H | OC(=O)C$_6$H$_3$-2,6(CH$_3$)$_2$ | H | 207d |
| 32 | H | OC(=O)C$_6$H$_4$-2CH$_3$ | H | 255 |
| 33 | H | OC(=O)CH$_2$C(CH$_3$)$_3$ | H | 234–236d |
| 34 | H | OC(=O)C(CH$_3$)$_2$(CH$_2$)$_2$CH$_3$ | H | 254–256 |
| 35 | H | OC(=O)CH$_2$CH(CH$_3$)$_2$ | H | 209–211 |
| 36 | H | OC(=O)(CH$_2$)$_8$CH$_3$ | H | 162–164 |
| 37 | H | OC(=O)O(CH$_2$)$_7$CH$_3$ | H | 171–174 |
| 38 | C(=O)OC(CH$_3$)$_3$ | OC(=O)C(CH$_3$)$_3$ | H | 194d |
| 39 | H | OC(=O)C$_6$H$_4$-4CF$_3$ | H | 148–150* |
| 40 | H | OC(=O)C(CH$_3$)$_2$CH$_2$CH$_3$ | H | 235–238 |
| 41 | H | OCH$_2$CH$_2$OH | H | 210–212d |

*Lit, m.p. 220–222
[a] isolated as free base

EXAMPLE 1

6-O-Demethylgalanthamine

To a stirred solution of 20 ml of dry DMF at −40° under nitrogen was added 0.57 ml (0.48 g) of ethanethiol. The mixture was stirred for several minutes at −40° to −30° after which 2.84 ml of 2.5 M BuLi in hexanes was added slowly by syringe at −40° to −50°. The solution was then allowed to warm to room temperature over 15 minutes, heated to 50° under aspirator vacuum and again cooled to 30°. To the oil was dissolved in chloroform, shaken with NH$_4$Cl, made basic with aq NaHCO$_3$ and extracted four times with CHCl$_3$. The pH of the aqueous layer was then adjusted to 9–10 with NH$_4$OH and again extracted four times with chloroform. The combined organic extracts were dried (Na$_2$SO$_4$), filtered and concentrated to an oil. The oil was dissolved in degassed 5% methanol/chloroform and flash chromatographed on silica gel eluting with the same solvent system followed by 10% methanol/chloroform to provide a beige solid. The material was dissolved in acetone and allowed to crystallize overnight to provide 0.298 g of (6-O-demethyl) galanthamine, m.p. 225–229°.

ANALYSIS:

| Calculated for $C_{16}H_{19}NO_3$: | 70.31% C | 7.01% H | 5.12% N |
|---|---|---|---|
| Found: | 70.14% C | 7.29% H | 4.96% N |

EXAMPLE 2

6-O-Demethyl[3-O,6-O-bis-(1-methylethyl) carbonyl]galanthamine hydrochloride hydrate To a cold solution of 6-O-demethylgalanthamine (0.5 g) in 125 ml of dichloromethane was added 4dimethylaminopyridine (1.2 g) followed by a solution of isobutyric anhydride (1.0 ml) in 5 ml of dichloromethane. After stirring at 0° C. for one hour, then at ambient temperature for one hour, the solution was evaporated to an oil, which was dissolved in ethyl acetate, washed with water, sodium carbonate, saturated sodium chloride solution, then dried over anhydrous sodium sulfate. After filtering, the solvents were evaporated to an oil (0.7 g) which was eluted on a silica gel column with 10% methanol/dichloromethane via HPLC to yield a thick yellow oil (0.5 g) which was dissolved in ether, and the pH adjusted to 1 with ethereal HCl. The resultant precipitate was collected and dried to give an off-white solid which was recrystallized from methanol/ether (1:10) to yield 0.35 g, m.p. 225° C. (dec.)

ANALYSIS:

| Calculated for $C_{24}H_3NO_5 \cdot HCl \cdot H_2O$: | 61.59% C | 7.32% H | 2.99% N |
|---|---|---|---|
| Found: | 61.53% C | 7.34% H | 2.97% N |

EXAMPLE 3

6-O-Demethyl-6-O-(t-butylcarbonyl)galanthamine hydrochloride

To a stirred suspension of 1.0 g of 6-O-demethylgalanthamine in 6.5 ml of chloroform was added 0.74 ml (0.68 g) of trimethylacetic anhydride followed by 45 mg of 4-dimethylaminopyridine. The mixture was stirred at room temperature for 4 hours. The solution as poured onto a flash chromatography column packed with 3% methanol/chloroform and eluted with the same solvent system followed by 5% methanol/chloroform. The product-containing fractions were combined and concentrated to provide a white solid (quantitative yield). The material was recrystallized from cyclohexane, filtered, dried, dissolved in ether and the hydrochloride salt precipitated by addition of ethereal HCl. The salt was isolated by filtration and dried to provide 0.421 g of 6-O-demethyl-6-O-(t-butylcarbonyl) galanthamine hydrochloride, m.p. 250–251° C.

ANALYSIS:

| Calculated for $C_{21}H_{27}NO_4 \cdot HCl$: | 64.03% C | 7.16% H | 3.56% N |
|---|---|---|---|
| Found: | 63.99% C | 7.21% H | 3.44% N |

EXAMPLE 4

6-O-Demethyl-[3-O,6-O-bis-(ethylcarbonyl)] galanthamine hydrochloride

To a cold solution of 6-O-demethylgalanthamine (1.5 g) in 100 ml of dichloromethane, was added 4-dimethylaminopyridine (3.5 g) followed by slow addition of a solution of propionic anhydride (2.4 ml) in 10 ml of dichloromethane. After stirring at ambient temperature for one hour, the mixture was evaporated to a yellow oil which was dissolved in ethyl acetate. The solution was washed with water, sodium carbonate solution, saturated sodium chloride solution and then dried over anhydrous $MgSO_4$. After filtering, the solvent was evaporated to a yellow oil, 2.0 g, which was eluted on a silica gel column with 5% methanol/dichloromethane via flash chromatography. The desired fractions were combined and evaporated to a thick yellow oil, 1.8 g. This oil was dissolved in ether and adjusted to pH 1 with ethereal-HCl. The resultant white precipitate was collected and dried to give 1.8 g of the product, m.p. 170–172° C.

ANALYSIS:

| Calculated for $C_{22}H_{27}NO_5 \cdot HCl$: | 62.62% C | 6.69% H | 3.32% N |
|---|---|---|---|
| Found: | 62.19% C | 6.65% H | 3.16% N |

EXAMPLE 5

6-O-Demethyl-6-O-(acetyl)galanthamine hydrochloride

To a stirred suspension of 1.02 g of 6-O-demethylgalanthamine in 6.0 ml of chloroform was added by syringe 0.35 ml of acetic anhydride followed by 45.5 mg of DMAP dissolved in 0.5 ml of chloroform. The suspension was allowed to stir for 3.5 hours at room temperature after which it was filtered onto a flash chromatography column, packed with silica gel in 5% methanol:chloroform, and eluted with the same solvent system. The product-containing fractions were combined and concentrated to a yellow oil which was crystallized from ethyl ether to provide 0.44 g of a white solid. The solid was dissolved in chloroform, diluted with ethyl ether and the hydrochloride salt was precipitated by addition of ethereal hydrogen chloride to provide 0.47 g of 6-O-demethyl-6-O-(acetyl)galanthamine hydrochloride which was recrystallized from acetonitrile, m.p. 244–246° C. (dec).

ANALYSIS:

| Calculated for $C_{18}H_{21}NO_4 \cdot HCl$: | 61.45% C | 6.30% H | 3.98% N |
|---|---|---|---|
| Found: | 60.97% C | 6.34% H | 3.86% N |

EXAMPLE 6

6-O-Demethyl-3-O,6-O-bis-(acetyl)galanthamine hydrochloride

To a cold solution of 6-O-demethyl-galanthamine (2.0 g) in 75 ml of dichloromethane, was added 4-dimethylaminopyridine (4.6 g) followed by a solution of acetic anhydride (2.3 ml). After stirring at ambient temperature for 5 hours, the solution was eluted on a silica gel column with 3% methanol/dichloromethane via HPLC. The desired fractions were combined and then evaporated to a thick yellow oil (2.1 g). A sample (0.5 g) of this oil was dissolved in methanol then acidified to pH 1 with ethereal-HCl; followed by dilution with ether. The resultant white precipitate was collected and dried to give 0.4 g, 142° C. dec.

ANALYSIS:

| | | | |
|---|---|---|---|
| Calculated for $C_{20}H_{23}NO_5 \cdot HCl$: | 60.99% C | 6.14% H | 3.56% N |
| Found: | 60.78% C | 6.08% H | 3.48% N |

EXAMPLE 7

6-O-Demethyl-3-O-(acetyl)galanthamine hydrochloride

To a solution of 6-O-demethyl-3-O,6-O-bis-(acetyl) galanthamine (EXAMPLE 6) 1.5 g in 30 ml methanol was added 5 ml of a saturated solution of sodium bicarbonate. After stirring at ambient temperature for twenty hours, the mixture was poured into 100 ml water, stirred for five minutes, then extracted with dichloromethane. The dichloromethane layer was washed with water, saturated NaCl solution, then dried over anhydrous $MgSO_4$. After filtering, the solvent was evaporated to a tan solid, 1.35 g, 215° C. dec. This material was dissolved in methanol, then acidified to pH 1 with ethereal-HCl; followed by dilution with ether. The resultant white precipitate was collected and dried to give 1.0 g, m.p. 162° C. (dec).

ANALYSIS:

| | | | |
|---|---|---|---|
| Calculated for $C_{18}H_{21}NO_4 \cdot HCl$: | 61.44% C | 6.30% H | 3.98% N |
| Found: | 61.53% C | 6.56% H | 4.21% N |

EXAMPLE 8

6-O-Demethyl-[3-O,6-O-bis-(t-butylcarbonyl) galanthamine hydrochloride

To a cold solution of 6Odemethylgalanthamine 1.5 g in 100 ml of dichloromethane, was added 4-dimethylaminopyridine (3.5 g) followed by a solution of trimethylacetic anhydride (3.8 ml) in 10 ml of dichloromethane. After stirring at ambient temperature for one hour, the solution was evaporated to a yellow oil. A solution of the oil and ethyl acetate was washed with water, sodium carbonate solution, saturated sodium chloride solution, and then dried over anhydrous $MgSO_4$. After filtering, the solvent was evaporated to afford a yellow solid, which was eluted on a silica gel column with 2% methanol/dichloromethane via flash chromatography. The desired fractions were combined and evaporated to give a white solid, 1.6 g, m.p. 117–119° C. A solution of the solid and ether was adjusted to pH 1 with ethereal-HCl, and the resultant white precipitate was collected and dried to give 1.4 g of product, m.p. 265° C. (dec).

ANALYSIS:

| | | | |
|---|---|---|---|
| Calculated for $C_{26}H_{35}NO_5 \cdot HCl$: | 65.33% C | 7.59% H | 2.93% N |
| Found: | 64.85% C | 7.67% H | 2.68% N |

EXAMPLE 9

6-O-Demethyl-6-O-(prop-2-yl-oxycarbonyl) galanthamine hydrochloride

To a cold solution of 6-O-demethylgalanthamine 1.5 g in 60 ml of dichloromethane, was added triethylamine (0.8 ml) followed by a solution of isopropyl chloroformate (1.0 M solution in toluene, 5.5 ml). After stirring at 0° C. for one hour, the mixture was stirred at ambient temperature for twenty hours. The mixture was added to a flash silica gel column and eluted with 10% methanol/dichloromethane. The desired fractions were combined and evaporated to a thick yellow oil, 0.5 g. This oil was dissolved in methanol/ether (1:10) and then acidified to pH 1 with ethereal-HCl. The resultant white precipitate was collected and dried, to give 0.4 g of product, m.p. 218° C. (dec.).

ANALYSIS:

| | | | |
|---|---|---|---|
| Calculated for $C_{20}H_{25}NO_5 \cdot HCl$: | 60.67% C | 6.62% H | 3.54% N |
| Found: | 61.15% C | 6.56% H | 3.44% N |

EXAMPLE 10

6-O-Demethyl-3-O-(prop-2-yl-carbonyl-6-O-(t-butylcarbonyl)galanthamine hydrate hydrochloride To a solution of 6-O-demethyl-6-O-(t-butylcarbonyl) galanthamine (EXAMPLE 9) (2.6 g) in 100 ml of dichloromethane was added 4-dimethyl-aminopyridine (0.9 g) followed by a solution of isobutyric anhydride (1.2 ml in 10 ml of dichloromethane). After stirring at ambient temperature for twenty hours, the mixture was added to a silica gel column and eluted with 3% methanol/dichloromethane via HPLC. The desired fractions were combined and then evaporated to a clear thick oil (2.0 g). A solution of the oil was adjusted to pH 1 in ether with ethereal-HCl. The resultant white precipitate was collected and dried to give 1.8 g of product, m.p. 248° C. (dec.).

ANALYSIS:

| | | | |
|---|---|---|---|
| Calculated for $C_{25}H_{33}NO_5 \cdot HCl$: | 62.29% C | 7.53% H | 2.91% N |
| Found: | 62.42% C | 7.32% H | 2.76% N |

EXAMPLE 11

6-O-Demethyl-6-O-(benzoyl)galanthamine

To a stirred suspension of 0.8 g of 6-O-demethylgalanthamine, 8 ml of chloroform and 0.72 g of benzoic anhydride was added 0.44 ml of 1,8-diazabicyclo-[5.4.0]undec-7-ene. The mixture was stirred at room temperature for 4 hours and subsequently poured onto a flash chromatography column packed with silica gel in 3% methanol/chloroform. The column was eluted with the same solvent system followed by 5% methanol/chloroform. The product-containing fractions were combined and concentrated to provide an oil which was crystallized from ether to give 0.45 g of 6-O-demethyl-6-benzoylgalanthamine, m.p. 144–145° C.

ANALYSIS:

| | | | |
|---|---|---|---|
| Calculated for $C_{22}H_{23}NO_4$: | 73.19% C | 6.14% H | 3.71% N |
| Found: | 73.29% C | 6.11% H | 3.79% N |

EXAMPLE 12

6-O-Demethyl-6-O-(t-butylcarbonyl)-3-O-(n-heptylcarbonyl)galanthamine hemihydrate hydrochloride To a cold solution of 6-O-demethyl-6-O-(t-butylcarbonyl) galanthamine (EXAMPLE 11) 2.6 g in 100 ml dichloromethane, was added 4-dimethylaminopyridine (1.0 g) followed by a solution of n-octanoic anhydride (2.4 ml) in 10 ml dichloromethane. After stirring at ambient temperature for twenty hours, the mixture was eluted on a silica gel column with 3% methanol/dichloromethane via HPLC. The desired fractions were combined, then evaporated to a clear thick oil, which solidified to a white solid upon cooling to give 3.0, m.p. 27° C. This solid was dissolved in methanol, and the solution was adjusted to pH 1 with ethereal-HCl, then diluted with ether. The resultant white precipitate was collected and dried to give 2.0 g, m.p. 185–187° C.

ANALYSIS:

| | | | |
|---|---|---|---|
| Calculated for $C_{29}H_{41}NO_5 \cdot HCl \cdot 0.5H_2O$: | 65.83% C | 8.19% H | 2.65% N |
| Found: | 65.98% C | 8.13% H | 2.65% N |

EXAMPLE 13

6-O-Demethyl-3-O,6O-bis-(n-heptylcarbonyl) galanthamine hydrochloride hemihydrate To a cold solution of 6-O-demethylgalanthamine 1.5 g in 75 ml of dichloromethane, was added 4-diemthylaminopyridine (3.5 g) followed by a solution of octanoic anhydride (5.6 ml) in 25 ml dichloromethane. After stirring at ambient temperature for twenty hours, the mixture was eluted on a silica gel column with 3% methanol:dichloromethane via HPLC. The desired fractions were combined, then evaporated to a thick yellow oil, 2.3 g. This oil was dissolved in methanol, and the pH adjusted to 1 with ethereal:HCl; then diluted with ether. The resultant white precipitate was collected and dried to give 2.0 g, 215° C. dec.

ANALYSIS:

| | | | |
|---|---|---|---|
| Calculated for $C_{32}H_{47}NO_5 \cdot HCl \cdot 0.5H_2O$: | 67.28% C | 8.65% H | 2.45% N |
| Found: | 67.01% C | 8.91% H | 2.25% N |

EXAMPLE 14

6-O-Demethyl-3-O,6-O-bis-(t-butoxycarbonyl) galanthamine hydrochloride

To a cold solution of 6-O-demethylgalanthamine (1.0 g in 50 ml dichloromethane), was added 4-dimethylaminopyridine (2.3 g) followed by a solution of di-t-butyl dicarbonate (2.9 ml) in 20 ml of dichloromethane. After stirring at ambient temperature for forty hours, the mixture was eluted on a silica gel column with 3% methanol/dichloromethane via HPLC. The desired fractions were combined, then evaporated to a thick yellow oil, 1.3 g. The oil was dissolved in methanol, and the pH was adjusted to 1 with ethereal-HCl, then diluted with ether. The resultant white precipitate was collected and dried to give 1.2 g, 154° C. dec.

ANALYSIS:

| | | | |
|---|---|---|---|
| Calculated for $C_{26}H_{35}NO_7 \cdot HCl$: | 61.23% C | 7.12% H | 2.75% N |
| Found: | 60.83% C | 7.10% H | 2.72% N |

EXAMPLE 15

7-Bromo-6-O-demethylgalanthamine

To a stirred solution of 1.38 ml (0.966 g) of t-butylamine in 36 ml of azeotripically dried toluene at −20 to −30° C. was added dropwise 0.34 ml (1.05 g) of bromine such that the temperature remained between −20 to −30° C. The solution was then cooled to −70 to −75° C. and a solution of 3.0 g of 6-demethylgalanthamine in 15 ml of DMF was added slowly such that the temperature did not rise above −70° C. The solution was stirred for 2 hours at −70 to −78° C. and subsequently allowed to warm slowly to room temperature over 6 hours. The solution was again cooled to 0° C., poured into ice/$NaHCO_3$/water, and extracted with chloroform. The aqueous fraction was saturated with NaCl and extracted 3 times with chloroform. The chloroform extracts were dried ($Na_2SO_4$), filtered and concentrated to an oil which was purified by HPLC, employing a Water Prep 500 Instrument and eluting with 3% methanol/chloroform, followed by 5% methanol/chloroform. The pure product-containing fractions were combined and concentrated to provide 1.83 g (47.3% based on 6-demethylgalanthamine, 78.9% based on bromine, the limiting reagent). Crystallization from acetone provided analytically pure 7-bromo-6-0-demethyl galanthamine, m.p. 138–141° C.

ANALYSIS:

| | | | |
|---|---|---|---|
| Calculated for $C_{16}H_{18}BrNO_3$: | 54.56% C | 5.15% H | 3.98% N |
| Found: | 54.62% C | 5.50% H | 3.61% N |

EXAMPLE 16

7-Bromo-6-O-demethyl-6-O-(t-butylcarbonyl) galanthamine hydrochloride

To a stirred suspension of a mixture of approximately 0.528 g of 7-bromo- 6-O-demethylgalanthamine and 93.2 mg of 6-O-demethylgalanthamine in 4 ml of chloroform was added 0.37 ml (0.34 g) of pivalic anhydride followed by 23 mg of DMAP. The mixture was stirred at room temperature for 5 hours. The solution was poured onto a flash chromatography column packed with 3% methanol/chloroform and eluted with the same solvent system followed by 5% methanol/chloroform. The product-containing fractions were combined and concentrated to a white solid. The material was dissolved in ether, decanted and the hydrochloride salt precipitated by addition of ethereal HCl. The material was isolated by filtration dried at 80° C. under vacuum to provide 0.315 g of 7-bromo-6-O-demethyl-6-O-(t-butylcarbonyl)-galanthamine, m.p. 275–278° C.

ANALYSIS:

| Calculated for $C_{21}H_{26}BrNO_4$: | 53.35% C | 5.76% H | 2.96% N |
|---|---|---|---|
| Found: | 53.37% C | 5.41% H | 2.79% N |

EXAMPLE 17

6-O-Demethyl-6-O-(ethylcarbonyl)galanthamine hydrochloride

To a stirred suspension of 1.00 g of 6-O-demethylgalanthamine in 6.5 ml of chloroform was added 0.47 ml of propionic anhydride followed by 45.2 mg of DMAP dissolved in 0.5 ml of chloroform. The suspension was allowed to stir at room temperature overnight and filtered onto a flash chromatography column, packed with silica gel and 3% methyl alcohol:chloroform and eluted with the same solvent system followed by 5% methyl alcohol:chloroform. The product-containing fractions were combined and concentrated to provide a yellow solid. Recrystallization from cyclohexane gave 0.70 g. Precipitation of the hydrochloride salt using ethereal hydrogen chloride gave 0.74 g of 6-O-demethyl-6-O-(ethylcarbonyl)galanthamine hydrochloride which was recrystallized from acetonitrile, m.p. 221–223° C.

ANALYSIS:

| Calculated for $C_{19}H_{23}NO_4.HCl$: | 62.38% C | 6.61% H | 3.83% N |
|---|---|---|---|
| Found | 62.32% C | 6.67% H | 3.89% N |

EXAMPLE 18

6-O-Acetyl-7-bromo-6-O-demethylgalanthamine hydrochloride

To a stirred solution of 0.851 g of 7-bromo-6-demethylgalanthamine in 2 ml of chloroform was added 0.227 ml (0.245 g) of acetic anhydride followed by 29.6 mg of 4-dimethylaminopyridine. The solution was stirred at room temperature for 3 hours. The mixture was then poured onto a flash silica gel column packed with silica gel in 3% methanol/chloroform. The column was eluted with the same solvent system followed by 5% methanol/chloroform. The pure product-containing fractions were combined, concentrated to an oil and crystallized from ether to provide 0.455 g of colorless crystals. The material was dissolved in chloroform/ether and the hydrochloride salt precipitated by addition of ethereal hydrogen chloride, isolated by filtration and dried to provide 335 mg of 6acetyl-7-bromo-6-O-demethylgalanthamine hydrochloride, m.p. 236–238° C.

ANALYSIS:

| Calculated for $C_{18}H_{20}BrNO_4$: | 50.19% C | 4.91% H | 3.25% N |
|---|---|---|---|
| Found: | 49.83% C | 4.65% H | 3.09% N |

EXAMPLE 19

6-O-Demethyl-6-O-(methoxycarbonyl)galanthamine hydrochloride

To a cold solution of 6-O-demethylgalanthamine (1.5 g) in 60 ml dichloromethane, was added 4-dimethylaminopyridine (0.7 g); followed by a solution of dimethyl pyrocarbonate (0.6 ml) in 10 ml of dichloromethane. After stirring at ambient temperature for 4 hours, the solution was eluted on a silica gel column with 3% methanol/dichloromethane via HPLC. The desired fractions were combined, then evaporated to a thick clear oil, 1.0 g. This oil was dissolved in methanol, then acidified to pH 1 with ethereal-HCl, followed by dilution with ether. The resultant white precipitate was collected and dried to give 1.0 g, 195° C. dec.

ANALYSIS:

| Calculated for $C_{18}H_{21}NO_5.HCl$: | 58.77% C | 6.03% H | 3.81% N |
|---|---|---|---|
| Found: | 58.54% C | 6.20% H | 3.74% N |

EXAMPLE 20

6-O-Demethyl-6-O-(ethoxycarbonyl)galanthamine hydrochloride

To a cold solution of 6-O-demethylgalanthamine (1.5 g) in 60 ml dichloromethane, was added 4-dimethylaminopyridine (0.7 g) followed by a solution of diethyl pyrocarbonate (0.8 ml) in 10 ml of dichloromethane. After stirring at ambient temperature for 4 hours, the solution was eluted on a silica gel column with 3% methanol/dichloromethane via HPLC. The desired fractions were combined, then evaporated to a white solid, 1.8 g, m.p. 139–141° C. This material was dissolved in methanol then acidified to pH 1 with ethereal-HCl, followed by dilution with ether. The resultant white precipitate was collected and dried to give 1.3 g, 208° C. dec.

ANALYSIS:

| Calculated for $C_{19}H_{23}NO_5.HCl$: | 59.76% C | 6.33% H | 3.67% N |
|---|---|---|---|
| Found: | 59.74% C | 6.32% H | 3.44% N |

EXAMPLE 21

6-O-Demethyl-6-O-(t-butoxycarbonyl)galanthamine hydrochloride

To a cold solution of 6-O-demethyl-galanthamine (1.5 g) in 60 ml of dichloromethane was added 4-dimethylaminopyridine (0.7 g) followed by a solution of di-t-butyl dicarbonate (1.3 ml) in 10 ml dichloromethane. After stirring at ambient temperature for 4 hours, the solution was eluted on a silca gel column with 3% methanol/dichloromethane via HPLC. The desired fractions were combined and evaporated to a white solid, 1.9 g, m.p. 147–149° C. This solid was dissolved in methanol, acidified to pH 1 with ethereal-HCl then diluted with ether. The resultant white precipitate was collected and dried to give 1.3 g, 237° C. dec.

ANALYSIS:

| Calculated for $C_{21}H_{27}NO_5$·HCl: | 61.53% C | 6.88% H | 3.42% N |
|---|---|---|---|
| Found: | 61.62% C | 6.49% H | 3.36% N |

EXAMPLE 22

6-O-Demethyl-6-O-(n-heptylcarbonyl)galanthamine hydrochloride

To a mixture of 0.80 g (2.93 mmol) of 6-O-demethylgalanthamine and 0.82 g (5.92 mmol) of milled potassium carbonate was added 13.5 ml of dry THF. The suspension was cooled to 0° C. after which was added 1.10 ml (3.70 mmol) of octanoic anhydride. The reaction mixture was stirred at 0° C. for 1/2 hour followed by 3 hours at room temperature after which the suspension was filtered onto a flash chromatography column packed with silica gel and 3% methanol:chloroform and eluted with the same solvent system followed by 5% dry methyl alcohol:chloroform. The pure, product-containing fractions were combined and concentrated to provide 0.88 g (2.20 mmol; 75.3%) of the free base as an oil. The oil was dissolved in ethyl ether and the hydrochloride salt precipitated by addition of ethereal hydrogen chloride to give 0.51 g of 6-O-demethyl-6-O-(n-heptylcarbonyl)galanthamine hydrochloride, m.p. 158–161° C.

ANALYSIS:

| Calculated for $C_{24}H_{33}NO_4$·HCl: | 66.12% C | 7.86% H | 3.21% N |
|---|---|---|---|
| Found: | 66.01% C | 7.75% H | 3.67% N |

EXAMPLE 23

6-O-Demethyl-6-O-(n-butylcarbonyl)galanthamine hydrochloride

To a stirred suspension of 1.00 g (3.6 mmol) of 6-O-demethylgalanthamine dissolved in 10.0 ml of chloroform was added a solution of 0.45 g (3.66 mmol) of 4-dimethylaminopyridine dissolved in 6.0 ml of chloroform by syringe, followed by 0.69 ml (3.49 mmol) of valeric anhydride dissolved in 4.0 ml of chloroform via syringe. The reaction mixture was stirred at room temperature for 0.5 hour after which it was poured onto a flash chromatography column packed with silica gel and 3% methanol:chloroform and eluted with the same solvent system, followed by 5% methanol:chloroform. The appropriate fractions were combined and concentrated to a clear, yellow oil. The oil was dissolved in diethyl ether and the hydrochloride salt precipitated by addition of ethereal hydrogen chloride to provide 0.73 g (1.85 mmol; 51%) of 6-O-demethyl-6-O-(n-butylcarbonyl)galanthamine hydrochloride, m.p. 208–210° C.

ANALYSIS:

| Calculated for $C_{21}H_{28}NO_4$·HCl: | 64.03% C | 7.16% H | 3.56% N |
|---|---|---|---|
| Found: | 63.91% C | 7.25% H | 3.48% N |

EXAMPLE 24

6-O-Demethyl-6-O-(n-pentylcarbonyl)galanthamine hydrochloride

To a stirred solution of 1.00 g (3.66 mmol) of &&demethylgalanthamine in 10.0 ml of chloroform was added 0.45 g (3.67 mmol) of 4dimethylaminopyridine dissolved in 4.0 ml of chloroform by syringe, followed by 0.80 ml (0.74 mmol) of hexanoic anhydride in 6.0 ml of chloroform via a syringe. The mixture was stirred at room temperature for 3.5 hours, poured onto a flash chromatography column packed with silica gel and 3% methanol:chloroform, and eluted with the same solvent system, followed by 5% methanol:chloroform. The appropriate fractions were combined and concentrated to a yellow oil weighing 1.26 g (3.39 mmol; 92%). The oil was dissolved in diethyl ether and the hydrochloride salt precipitated by addition of ethereal hydrogen chloride to give 0.77 g (1.87 mmol; 51%) of 6-O-demethyl-6-O-(n-pentyl-carbonyl)galanthamine hydrochloride, m.p. 212–215° C.

ANALYSIS:

| Calculated for $C_{22}H_{29}NO_4$·HCl: | 64.78% C | 7.41% H | 3.43% N |
|---|---|---|---|
| Found: | 64.66% C | 7.25% H | 3.37% N |

EXAMPLE 25

6-O-Demethyl-6-O-(n-hexylcarbonyl)galanthamine hydrochloride

To a stirred solution of 1.00 g (3.66 mmol) of 6-O-demethylgalanthamine in 10.0 ml of chloroform was added a solution of 0.45 g (3.69 mmol) of 4-dimethylaminopyridine in 4.0 ml of chloroform via syringe and stirred at room temperature for 20 minutes after which was added 0.91 ml (3.47 mmol) of n-heptanoic anhydride dissolved in 6.0 ml of chloroform by syringe. The reaction mixture was allowed to stir at room temperature for 0.5 hour, poured onto a flash chromatography column, packed with silica gel and 3% methanol:chloroform, and eluted with the same solvent system, followed by 5% methanol:chloroform. The pure, product containing fractions were combined and concentrated to a yellow oil weighing 1.14 g (2.95 mmol, 81%). The oil was dissolved in diethyl ether and the hydrochloride salt precipitated by addition of ethereal hydrogen chloride to provide 0.74 g (1.75 mmol; 48%) of 6-O-demethyl-6-O-(n-hexylcarbonyl)galanthamine hydrochloride, m.p. 178–180° C.

ANALYSIS:

| Calculated for C$_{23}$H$_{31}$NO$_4$.HCl: | 65.47% C | 7.64% H | 3.32% N |
|---|---|---|---|
| Found: | 65.18% C | 7.88% H | 3.18% N |

EXAMPLE 26

6-O-Demethyl-3-O-[2-(methyl)butan-2-yl-oxycarbonyl]-6-O-(acetyl)-galanthamine hydrochloride hydrate To a cold solution of 6-O-demethyl-6-O-(methylcarbonyl)galanthamine (Example 5, 2.8 g, 0.009 mole) and 4-dimethylaminopyridine (1.1 g, 0.009 mole) in 80 ml of dichloromethane, was added dropwise, a solution of di-t-amyl dicarbonate (2.2 ml, 0.009 mole) in 10 ml of dichloromethane.

After stirring at ambient temperature for 20 hours, the mixture was eluted on a silica gel column with 3% methanol/dichloromethane via HPLC. The desired fractions were combined and evaporated to a thick clear oil, 2.7 g (69%). A 0.4 g sample of this oil was dissolved in methanol, adjusted to pH 1 with etheral-HCl, and then diluted with ether. The resultant white precipitate was collected and dried to give 0.3 g (70%) of the product as a colorless solid, m.p. 178–180° C. (dec.).

ANALYSIS:

| Calculated for C$_{24}$H$_{31}$NO$_6$.HCl.H$_2$O: | 59.56% C | 7.08% H | 2.89% N |
|---|---|---|---|
| Found: | 59.84% C | 7.01% H | 3.02% N |

EXAMPLE 27

6-O-Demethyl-3-O-[2-(methyl)butan-2-yl-oxycarbonyl]galanthamine

To a solution of 6-O-demethyl-3-O-[2-(methyl)butan-2-yl-oxycarbonyl]-6-O-(acetyl)galanthamine (Example 26, 2.0 g, 0.0047 mole) in 25 ml of methanol was added 5 ml of a saturated solution of NaHCO$_3$ in water.

After stirring at ambient temperature for four hours, the mixture was poured into 100 ml of water, stirred for five minutes, and then extracted with dichloromethane (3×100 ml). The dichloromethane solution was washed with water, saturated NaCl solution, and dried over anhydrous MgSO$_4$.

After filtering, the filtrate was added to silica gel column and eluted with 5% methanol/dichloromethane via HPLC. The desired fractions were combined and evaporated to an off-white solid, which was triturated with hot ether to give the product as a white solid, 0.4 g (22%), m.p. 175° C. (dec.).

ANALYSIS:

| Calculated for C$_{22}$H$_{29}$NO$_5$: | 68.19% C | 7.54% H | 3.62% N |
|---|---|---|---|
| Found: | 67.99% C | 7.50% H | 3.52% N |

EXAMPLE 28

3-O-[2-Methyl)butan-2-yl-oxycarbonyl] galanthamine hydrate hydrochloride

To a cold solution of galanthamine (3.0 g, 0.01 mole) and 4-dimethylaminopyridine (1.2 g, 0.01 mole) in 80 ml of dichloromethane, was added dropwise a solution of di-t-butyl dicarbonate (2.4 ml, 0.01 mole) in 15 ml of dichloromethane.

After stirring at ambient temperature for forty-eight hours, the mixture was eluted on a silica gel column with 3% methanol/dichloromethane via HPLC. The desired fractions were combined and evaporated to a thick clear oil, 1.1 g (28%). This oil was dissolved in methanol, acidified to pH 1 with ethereal-HCl, and then diluted with ether. The precipitate was collected and dried to give 0.70 g (15%) of the product as a colorless solid, m.p. 167° C. (dec.).

ANALYSIS:

| Calculated for C$_{23}$H$_{31}$NO$_5$.H$_2$O.HCl: | 60.58% C | 7.52% H | 3.07% N |
|---|---|---|---|
| Found: | 60.68% C | 7.28% H | 3.48% N |

EXAMPLE 29

6-O-Demethyl-6-O-[(ethoxycarbonyl)methyl] galanthamine

To a suspension of 0.70 g (17.45 mmol) of sodium hydride (in 60% mineral oil) in 12.5 ml of tetrahydrofuran at room temperature was added, over 5–10 minutes, a solution of 5.00 g (18.29 mmol) of 6-O-demethylgalanthamine in 17.5 ml of N,N-dimethylformamide. The mixture was chilled in an ice bath and stirred at 0° C. for 20 minutes, after which solution of 2.03 ml (18.29 mmol) of ethyl bromoacetate in 5 ml of tetrahydrofuran was added slowly to the mixture which was stirred at room temperature for 1 hour. The resultant mixture was poured into ice-water and extracted twice with chloroform. The organic layers were combined, dried over sodium sulfate, filtered, and concentrated to a brown oil. The oil was dissolved in chloroform and chromatographed using a Waters Prep 500 HPLC, eluting with 2% methanol:chloroform, followed by 5% methanol:chloroform. The pure, product-containing fractions were combined and concentrated to a red oil, 6-O-demethyl-6-O-(ethoxycarbonyl)methylgalanthamine, 2.60 g .

ANALYSIS:

| Calculated for C$_{20}$H$_{25}$NO$_5$: | 66.84% C | 7.01% H | 3.90% N |
|---|---|---|---|
| Found: | 66.56% C | 6.86% H | 3.85% N |

EXAMPLE 30

6-O-Demethyl-6-O-[2-(methyl)butan-2-yl-oxycarbonyl]galanthamine hydrochloride

To a cold solution of 6-O-demethylgalanthamine (2.0 g, 0.007 mole) and 4-dimethylaminopyridine (0.85 g, 0.007 mole) in 70 ml of dichloromethane was added dropwise a solution of di-tert-amyl dicarbonate (.7 ml, 0.007 mole) in 10 ml of dichloromethane.

After stirring at ambient temperature for eight hours, the mixture was added to a silica gel column and eluted with 3% methanol/chloroform via HPLC. The desired fractions were evaporated in vacuo to a white solid, 2.2 g (85%), m.p. 129–130° C.

This material was dissolved in ether and adjusted to pH 1 with ethereal-HCl, to give a white solid, 1.8 g (63%), m.p. 205° C. (dec.).

ANALYSIS:

| | | | |
|---|---|---|---|
| Calculated for $C_{22}H_{29}NO_5 \cdot HCl$: | 62.33% C | 7.13% H | 3.34% N |
| Found: | 62.49% C | 7.16% H | 3.35% N |

EXAMPLE 31

6-O-Demethyl-6-O-(2.6dimethylphenylcarbonyl) galanthamine hydrochloride

To a cold solution of 6O-demethylgalanthamine (2.0 g, 0.007 mole), triethylamine (1.0 ml, 0.007 mole), and 4-dimethylaminopyridine (0.01 g) in 70 ml of dichloromethane, was added dropwise a solution of 2,6-dimethylbenzoyl chloride (1.2 g, 0.007 mole) in 10 ml of dichloromethane.

After stirring at ambient temperature for twenty hours, the mixture was added to a silica gel column and eluted with 3% methanol/dichloromethane via HPLC. The desired fractions were combined and evaporated in vacuo to a white solid, 2.7 g (95%), m.p. 159–161° C.

A 1.5 g sample of this material was dissolved in ethyl acetate and adjusted to pH 1 with etheral-HCl, to give a white solid, 1.1 g (81%), m.p. 207° C. (dec.).

ANALYSIS:

| | | | |
|---|---|---|---|
| Calculated for $C_{25}H_{27}NO_4 \cdot HCl$: | 67.94% C | 6.39% H | 3.17% N |
| Found: | 67.58% C | 6.63% H | 3.11% N |

EXAMPLE 32

6-O-Demethyl-6-O-(2-methylphenylcarbonyl) galanthamine hydrochloride

To a cold solution of 6-O-demethylgalanthamine (2.0 g, 0.007 mole), triethylamine (1.0 ml, 0.007 mole) and 4dimethylaminopyridine (0.01 g, 0.0001 mole) in 70 ml of dichloromethane, was added dropwise a solution of o-toluoyl chloride (0.9 ml, 0.007 mole) in 10 ml of dichloromethane.

After stirring at ambient temperature for three hours, the mixture was added to a silica gel column and eluted with 3% methanol/dichloromethane via HPLC. The desired fractions were combined and then evaporated to a white solid, 1.7 g (63%), m.p. 148–150° C.

A solution of the solid in ethyl acetate was adjusted to pH 1 with etheral-HCl, and the resultant white precipitate was collected and dried to give 1.2 g (40%) of product, m.p. 255° C. (dec.).

ANALYSIS:

| | | | |
|---|---|---|---|
| Calculated for $C_{24}H_{25}NO_4 \cdot HCl$: | 67.36% C | 6.12% H | 3.27% N |
| Found: | 67.62% C | 6.49% H | 3.09% N |

EXAMPLE 33

6-O-Demethyl-6-O-(2,2-dimethylpropylcarbonyl) galanthamine hydrochloride

To a stirred suspension of 1.00 g (3.66 mmol) of 6-O-demethylgalanthamine in 10.0 ml of chloroform was added 0.55 ml (3.67 mmol) of 1,8-diazabicyclo[5.4.0]undec-7-ene by syringe. The mixture was stirred in an ice bath for 10–15 minutes after which was added 0.55 ml (3.99 mmol) of t-butyl acetic acid via syringe. After the addition was complete, the suspension was allowed to warm to room temperature and stir at this temperature for 0.5 hour, poured into 50 ml of cold, saturated sodium bicarbonate solution and extracted with chloroform. To the aqueous layer was added sodium chloride and extracted twice with chloroform. The combined organic layers were dried over sodium sulfate, filtered, and concentrated to a yellow oil. The oil was dissolved in chloroform, filtered onto a flash chromatography column, packed with silica gel and 3% methanol:chloroform and eluted with the same solvent system, followed by 5% methanol:chloroform. The appropriate fractions were combined and concentrated to provide 0.61 g (1.64 mmol; 45%) of a white solid. The solid was dissolved in diethyl ether and the hydrochloride salt precipitated by addition of ethereal hydrogen chloride to provide 6-O-demethyl-6-O-(2,2-dimethyl-propylcarbonyl)galanthamine hydrochloride, m.p. 234–236° C. (dec).

ANALYSIS:

| | | | |
|---|---|---|---|
| Calculated for $C_{22}H_{29}NO_4 \cdot HCl$: | 64.78% C | 7.41% H | 3.43% N |
| Found: | 64.60% C | 7.65% H | 3.39% N |

EXAMPLE 34

6-O-Demethyl-6-O-[[(2-methyl)pentan-2-yl] carbonyl]galanthamine hydrochloride To a stirred suspension of 0.48 g (3.67 mmol) of 2,2-dimethylvaleric acid in 2.5 ml of chloroform was added 0.75 g (3.66 mmol) of 1,3dicyclohexylcarbodiimide dissolved in 0.7 ml of chloroform, followed by 1.00 g (3.66 mmol) of 6-O-demethylgalanthamine in 2.0 ml of chloroform, and 0.45 g (3.67 mmol) of 4-dimethylaminopyridine in 0.2 ml of chloroform. The suspension was stirred at room temperature for 6 hours after which it was filtered onto a flash chromatography column, packed with silica gel and 3% methanol:chloroform and eluted with the same solvent system, followed by 5% methanol:chloroform. The appropriate fractions were combined and concentrated to provide 0.68 g (1.78 mmol; 49%) of a yellow oil. The oil was dissolved in diethyl ether and the hydrochloride salt precipitated by addition of ethereal hydrogen chloride to provide 6-O-demethyl-6-O[[(2-methyl)pentan-2-yl]-carbonyl] galanthamine hydrochloride, m.p. 254–256° C. (dec.).

ANALYSIS:

| | | | |
|---|---|---|---|
| Calculated for $C_{23}H_{31}NO_4 \cdot HCl$: | 65.47% C | 7.64% H | 3.32% N |
| Found: | 65.60% C | 7.61% H | 3.32% N |

EXAMPLE 35

6-O-Demethyl-6-O-[2-(methyl)propylcarbonyl] galanthamine hydrochloride

To a stirred suspension of 0.80 g (2.91 mmol) of 6-O-demethylgalanthamine in 8 ml of chloroform was added 0.44 ml (2.94 mmol) of 1,8-diazabicyclo[5.4.0]undec-7-ene by syringe. The suspension was cooled in an ice bath for 10 minutes after which was added 0.38 ml (3.12 mmol) of isovaleryl chloride via syringe. The reaction mixture was warmed to room temperature, stirred at this temperature for 2 hours poured into a cold saturated solution of sodium bicarbonate and extracted with chloroform. The aqueous layer was treated with sodium chloride and extracted twice with chloroform. The combined organic extracts were dried over sodium sulfate, filtered, and concentrated to a yellow oil. The oil was dissolved in chloroform, pipetted onto a flash chromatography column, packed with silica gel in 3% methanol:chloroform, and eluted with the same solvent system, followed by 5% methanol:chloroform. The appropriate fractions were combined and concentrated to give 0.76 g (2.13 mmol; 73%) as an oil. The oil was dissolved in diethyl ether and chloroform and the hydrochloride salt precipitated by addition of ethereal hydrogen chloride to provide 6-O-demethyl-6-O-[2-(methyl)propylcarbonyl]galanthamine hydrochloride, m.p. 209–211° C. (dec.).

ANALYSIS:

| Calculated for $C_{21}H_{27}NO_4 \cdot HCl$: | 64.03% C | 7.16% H | 3.56% N |
|---|---|---|---|
| Found: | 63.79% C | 7.04% H | 3.45% N |

EXAMPLE 36

6-O-Demethyl-6-O-(n-nonylcarbonyl)galanthamine hydrochloride

To a stirred mixture of 1.99 g (7.29 mmol) of 6-O-demethylgalanthamine in 5.0 ml of dichloromethane was added 1.62 g (13.23 mmol) of 4-dimethylamino-pyridine, dissolved in 1.0 ml of dichloromethane. The mixture was cooled to 0° C. after which was added 3.13 g (9.50 mmol) of decanoic anhydride, dissolved in 0.5 ml of dichloromethane. The resultant mixture was stirred at room temperature for 1.5 hours after which it was cooled in an ice bath for 1.5 hours, warmed to room temperature and filtered onto a flash chromatography column, packed with silica gel and 3% methanol:chloroform and eluted with the same solvent system, followed by 5% methanol:chloroform. The appropriate fractions were combined and concentrated to provide a mixture of product and a slightly a higher eluting impurity as an oil. The oil was chromatographed on silica gel, eluting with 3% methanol:chloroform. The fractions containing the desired product were combined and concentrated to provide a slightly impure oil which was purified using Waters Prep 500 HPLC instrument, eluting with 2% methanol:chloroform. The pure, product-containing fractions were combined and concentrated to provide 1.78 g (4.16 mmol; 57%) of an oil. Precipitation of the hydrochloride salt using ethereal hydrogen chloride provided 6demethyl-6-O-(n-nonylcarbonyl)galanthamine hydrochloride, m.p. 162–164° C.

ANALYSIS:

| Calculated for $C_{26}H_{37}NO_4 \cdot HCl$: | 67.30% C | 8.25% H | 3.02% N |
|---|---|---|---|
| Found: | 67.28% C | 8.18% H | 2.84% N |

EXAMPLE 37

6-O-Demethyl-6-O-(n-octyloxycarbonyl)galanthamine hydrochloride

To a stirred suspension of 1.0 g (3.66 mmol) of 6-O-demethylgalanthamine in 10 ml of chloroform in an ice bath was added 0.49 ml (0.55 g, 3.65 mmol) of 1,8-diazabicyclo[5.4.0]undec-7-ene (DBU). To the solution was added by syringe 0.72 ml of n-octylchloroformate. The solution was stirred in an ice bath for 4.5 hours, poured into cold saturated sodium bicarbonate, extracted with ether and the aqueous layer treated with sodium chloride and extracted twice with ether. The combined ether extracts were dried ($Na_2SO_4$), filtered and concentrated to an oil which was purified by flash chromatography on silica gel, eluting with chloroform, followed by 3% methanol/chloroform. The pure, product-containing fractions were combined and concentrated to an oil (0.44 g, 0.102 mmol, 27.9%) which was dissolved in ether and the hydrochloride salt precipitated by addition of ethereal hydrogen chloride. The white solid was dried under vacuum at 80° C. to provide 0.27 g of 6-O-demethyl-6-O-(n-octyloxycarbonyl)galanthamine hydrochloride, m.p. 171–174° C.

ANALYSIS:

| Calculated for $C_{25}H_{35}NO_5 \cdot HCl$: | 64.43% C | 7.79% H | 3.01% N |
|---|---|---|---|
| Found: | 64.12% C | 7.86% H | 3.03% N |

EXAMPLE 38

6-O-Demethyl-3-O-(t-butoxycarbonyl)-6-O-(t-butylcarbonyl)galanthamine hydrochloride To a cold solution of 6-O-demethyl-6-O-(t-butylcarbonyl)galanthamine (2.2 g, 0.0062 mole) in 75 ml of dichloromethane was added 4-dimethylaminopyridine (0.85 g, 0.007 mole), followed by a solution of di-t-butyl carbonate (1.5 ml, 0.0062 mole) in 10 ml of dichloromethane.

After stirring at ambient temperature for 40 hours, the mixture was added to a silica gel column and eluted with 3% methanol:dichloromethane via HPLC. The desired fractions were evaporated to a thick yellow oil, 1.7 g (60%); which was dissolved in methanol, acidified to pH 1 with ethereal-HCl and then diluted with ether. The resultant white precipitate was collected and dried to give 1.1 g of the product, m.p. 194° C. (dec.).

ANALYSIS:

| Calculated for $C_{26}H_{35}NO_6 \cdot HCl$: | 63.21% C | 7.35% H | 2.84% N |
|---|---|---|---|
| Found: | 63.47% C | 7.42% H | 2.83% N |

EXAMPLE 39

6-O-Demethyl-6-O-(4-trifluoromethylphenylcarbonyl)galanthamine

To a cold solution of 6-O-demethylgalanthamine (1.7 g, 0.0062 mole) in 60 ml of dichloromethane was added triethylamine (0.9 ml, 0.0062 mole) and 4-dimethylaminopyridine (0.1 g, 0.001 mole), followed by a solution of 4-trifluoromethylbenzoyl chloride (0.9 ml, 0.0062 mole) in 10 ml of dichloromethane.

After stirring at ambient temperature for 20 hours, the mixture was added to a silica gel column and eluted with 3% methanol/dichloromethane via HPLC. The desired fractions were combined and evaporated to afford the product as a white solid, 2.6 g (90%), m.p. 148–150° C.

| ANALYSIS: | | | |
|---|---|---|---|
| Calculated for $C_{24}H_{22}F_3NO_4$: | 64.71% C | 4.98% H | 3.15% N |
| Found: | 64.45% C | 4.99% H | 3.02% N |

EXAMPLE 40

6-O-Demethyl-6-O-(2-methylbutan-2-yl-carbonyl) galanthamine hydrochloride

To a stirred solution of 0.46 ml (3.68mmol) of 2,2-dimethylbutyric acid in 3.7 ml of dry chloroform was added 1.01 g (3.70 mmol)of 6-O-demethylgalanthamine, followed by 0.76 g (3.67 mmol) of 1,3dicyclohexylcarbodiimide and 0.45 g (3.68 mmol) of dimethylaminopyridine. The reaction mixture was allowed to stir at room temperature for 23 hours, then filtered onto a flash chromatography column packed with silica gel in 3% methanol:chloroform and eluted with the same solvent system followed by 5% methanol:chloroform. The desired fractions were combined and concentrated to provide 1.07 g of an off-yellow solid. The solid was dissolved in ether and the hydrochloride salt was precipitated by the addition of ethereal hydrogen chloride to provide after drying material of m.p. 235–238° C. (dec).

| ANALYSIS: | | | |
|---|---|---|---|
| Calculated for $C_{22}H_{29}NO_4.HCl$: | 64.78% C | 7.41% H | 3.43% N |
| Found: | 64.63% C | 7.70% H | 3.54% N |

EXAMPLE 41

6-O-Demethyl-6-O-(2-hydroxyethyl)galathamine hemihydrate hydrochloride

To a solution of 4.6 ml (4.6 mmol) of lithium aluminum hydride (1M in tetrahydrofuran) was added a solution of 1.1 g (3.07 mmol) of 6-demethyl- 6-O-(ethoxycarbonylmethyl) galanthamine in 10.0 ml of tetrahydrofuran by syringe at 0° C. The solution was stirred at room temperature for 1 hour, cooled again to 0° C. for 10 min, quenched twice with 1.0 ml of distilled water, followed by 1.0 ml of 15% sodium hydroxide. The quenched reaction mixture was extracted three times with chloroform. The organic layers were combined, dried over sodium sulfate, filtered and concentrated to a white solid. The solid was dissolved in chloroform, filtered onto a flash chromatography column packed with silica gel in 5% methanol:chloroform, and eluted with the same solvent system. The appropriate fractions were combined and concentrated to a white solid (0.67 g). The solid was dissolved in diethyl ether and the hydrochloride salt was precipitated by addition of ethereal hydrogen chloride to provide 0.44 g of product, m.p.210–212° C. (dec).

| ANALYSIS: | | | |
|---|---|---|---|
| Calculated for $C_{18}H_{23}NO_4.HCl$: | 59.58% C | 6.94% H | 3.86% N |
| Found: | 59.13% C | 6.81% H | 3.81% N |

It should be understood that this specification and examples are set forth by way of illustration and limitation and that various modifications and changes may be made without departing from the spirit and scope of the present invention as defined by the appended claims.

We claim:

1. A compound of the formula

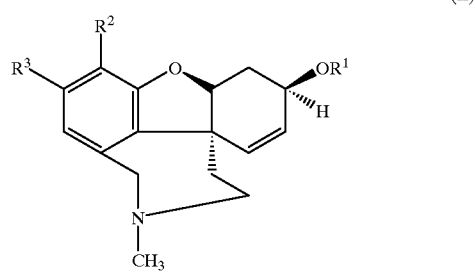

(II)

wherein $R^1$ is selected from the group consisting of hydrogen, $(C_1–C_{12})$alkylcarbonyl, $(C_1–C_{12})$alkoxycarbonyl and aryl$(C_1–C_{12})$alkylaminocarbonyl;

$R^2$ is selected from the group consisting of $(C_1–C_{12})$alkylcarbonyloxy, aryl$(C_1–C_4)$alkylcarbonyloxy, $(C_1–C_{12})$alkoxycarbonyloxy, arylcarbonyloxy, hydroxy, $(C_1–C_6)$alkoxycarbonyl$(C_1–C_6)$alkoxy and hydroxy$(C_1–C_{10})$alkoxy; and $R^3$ is hydrogen or bromo;

or a pharmaceutically acceptable acid addition salt thereof with the proviso that when $R^2$ is hydroxy, $R^1$ and $R^3$ are not both hydrogen or when $R^2$ is hydroxy and $R^3$ is hydrogen, $R^1$ is not $(C_1–C_{12})$alkylcarbonyl.

2. The compound of claim 1 wherein $R^1$ is selected from the group consisting of hydrogen, $(C_1–C_{12})$alkylcarbonyl and $(C_1–C_{12})$alkoxycarbonyl; and $R^2$ is selected from the group consisting of $(C_1–C_{12})$alkylcarbonyloxy, $(C_1–C_{12})$alkoxycarbonyloxy, arylcarbonyloxy, hydroxy, $(C_1–C_6)$alkoxycarbonyl $(C_1–C_6)$alkoxy and hydroxy$(C_1–C_6)$alkoxy.

3. The compound of claim 2 wherein $R^1$ is selected from the group consisting of hydrogen, $(C_1–C_8)$alkylcarbonyl and $(C_1–C_6)$alkoxycarbonyl; and $R^2$ is selected from the group consisting of hydroxy, $(C_1–C_{10})$alkylcarbonyloxy and arylcarbonyloxy.

4. The compound of claim 3 wherein $R^1$ is selected from the group consisting of hydrogen, methylcarbonyl, ethylcarbonyl, methylethylcarbonyl, t-butylcarbonyl and n-heptylcarbonyl; and $R^2$ is selected from the group consisting of methylcarbonyloxy, ethylcarbonyloxy, methylethylcarbonyloxy, t-butylcarbonyloxy and n-heptylcarbonyloxy, phenylcarbonyloxy, trifluoromethylphenylcarbonyloxy, methylphenylcarbonyloxy dimethylphenylcarbonyloxy and hydroxy.

5. The compound of claim 3 which is 6-O-demethyl[3-O,6-O-bis(prop-2-yl)-carbonyl]galanthamine or a pharmaceutically acceptable salt thereof.

6. The compound of claim 3 which is 6-O-demethyl-6-O-(t-butylcarbonyl)-galanthamine or a pharmaceutically acceptable acid salt thereof.

7. The compound of claim 3 which is 6-O-demethyl-[3-O,6-bis-(ethylcarbonyl)]galanthamine or a pharmaceutically acceptable acid salt thereof.

8. The compound of claim 3 which is 6-O-demethyl-6-O-(acetyl)galanthamine or a pharmaceutically acceptable acid salt thereof.

9. The compound of claim 3 which is 6-O-demethyl-3-O,6-bis-(acetyl)galanthamine or a pharmaceutically acceptable acid salt thereof.

10. The compound of claim 3 which is 6-O-demethyl-[3-O,6-O-bis-(t-butylcarbonyl)galanthamine or a pharmaceutically acceptable acid salt thereof.

11. The compound of claim 3 which is 6-O-demethyl-3-O-(prop-2-ylcarbonyl)-6-O-(t-butylcarbonyl)galanthamine or a pharmaceutically acceptable acid salt thereof.

12. The compound of claim 3 which is 6-O-demethyl-6-O-(benzoyl)galanthamine or a pharmaceutically acceptable acid salt thereof.

13. The compound of claim 3 which is 6-O-demethyl-6-O-(t-butylcarbonyl)-3-O-(n-heptylcarbonyl)galanthamine or a pharmaceutically acceptable acid salt thereof.

14. The compound of claim 3 which is 6-O-demethyl-3-O,6-O-bis-(heptylcarbonyl)galanthamine or a pharmaceutically acceptable acid salt thereof.

15. The compound of claim 3 which is 7-bromo-6-O-demethyl-6-O-(t-butylcarbonyl)galanthamine or a pharmaceutically acceptable acid salt thereof.

16. The compound of claim 3 which is 6-O-demethyl-6-O-(ethylcarbonyl)galanthamine or a pharmaceutically acceptable acid salt thereof.

17. The compound of claim 3 which is 6-O-demethyl-6-O-(n-heptylcarbonyl)galanthamine or a pharmaceutically acceptable acid salt thereof.

18. The compound of claim 3 which is 6-O-demethyl-6-O-(n-butylcarbonyl)galanthamine or a pharmaceutically acceptable acid salt thereof.

19. The compound of claim 3 which is 6-O-demethyl-6-O-(n-pentylcarbonyl)galanthamine or a pharmaceutically acceptable acid salt thereof.

20. The compound of claim 3 which is 6-O-demethyl-6-O-(n-hexylcarbonyl)galanthamine or a pharmaceutically acceptable acid salt thereof.

21. The compound of claim 3 which is 6-O-demethyl-6-O-(2,6-dimethylphenylcarbonyl)galanthamine or a pharmaceutically acceptable acid salt thereof.

22. The compound of claim 3 which is 6-O-demethyl-6-O-(2-methylphenylcarbonyl)galanthamine or a pharmaceutically acceptable acid salt thereof.

23. The compound of claim 3 which is 6-O-demethyl-6-O-(2,2-dimethyl-propylcarbonyl)galanthamine or a pharmaceutically acceptable acid salt thereof.

24. The compound of claim 3 which is 6-O-demethyl-6-O-[[(2-methyl)pentan-2-yl]carbonyl]galanthamine or a pharmaceutically acceptable acid salt thereof.

25. The compound of claim 3 which is 6-O-demethyl-6-O-[2-(methyl)propylcarbonyl]galanthamine or a pharmaceutically acceptable acid salt thereof.

26. The compound of claim 3 which is 6-O-demethyl-6-O-(n-nonylcarbonyl)galanthamine or a pharmaceutically acceptable acid salt thereof.

27. The compound of claim 3 which is 6-O-acetyl-7-bromo- 6-O-demethylgalanthamine or a pharmaceutically acceptable acid salt thereof.

28. The compound of claim 3 which is 6-O-demethyl-6-O-(4-trifluoromethylphenylcarbonyl)galanthamine or a pharmaceutically acceptable acid salt thereof.

29. The compound of claim 3 which is 7-bromo-6-O-demethylgalanthamine or a pharmaceutically acceptable acid addition salt thereof.

30. The compound of claim 3 which is 6-O-demethyl-6-O-(2-(methyl)butan-2-yl-carbonyl)galanthamine or a pharmaceutically acceptable acid addition salt.

31. The compound claim 2 wherein
$R^1$ is hydrogen, $(C_1-C_{12})$alkylcarbonyl or $(C_1-C_{12})$alkoxycarbonyl;
$R^2$ is $(C_1-C_{12})$alkoxycarbonyloxy; and
$R^3$ is hydrogen or bromo.

32. The compound of claim 31 wherein
$R^1$ is hydrogen, $(C_1-C_{10})$alkylcarbonyl or $(C_1-C_6)$alkoxycarbonyl;
$R^2$ is $(C_1-C_{10})$alkoxycarbonyloxy; and
$R^3$ is hydrogen or bromo.

33. The compound of claim 32 wherein
$R_1$ is hydrogen, methylcarbonyl or t-butoxycarbonyl;
$R^2$ is methoxycarbonyloxy, ethoxycarbonyloxy or t-butoxycarbonyloxy; and
$R^3$ is hydrogen.

34. The compound of claim 32 which is 6-O-demethyl-6-O-(n-octyloxycarbonyl)galanthamine or a pharmaceutically acceptable acid salt thereof.

35. The compound of claim 32 which is 6-O-demethyl-6-O-(prop-2-yloxycarbonyl)galanthamine or a pharmaceutically acceptable acid addition salt thereof.

36. The compound of claim 32 which is 6-O-demethyl-3-O,6-O-bis-(t-butoxycarbonyl)galanthamine or a pharmaceutically acceptable acid addition salt thereof.

37. The compound of claim 32 which is 6-O-demethyl-6-O-(methoxycarbonyl)-galanthamine or a pharmaceutically acceptable acid addition salt thereof.

38. The compound of claim 32 which is 6-O-demethyl-6-O-(ethoxycarbonyl)-galanthamine or a pharmaceutically acceptable acid addition salt thereof.

39. The compound of claim 32 which is 6-O-demethyl-6-(t-butoxycarbonyl)-galanthamine or a pharmaceutically acceptable acid addition salt thereof.

40. The compound of claim 3 which is 6-O-demethyl[2-(methyl)butan-2-yloxycarbonyl]-6-O-(acetyl)galanthamine or a pharmaceutically acceptable salt thereof.

41. A method of treating memory dysfunction characterized by decreased cholinergic function with 6-O-demethylgalanthamine which comprises administering to a mammal an acetylcholinesterase inhibiting amount of the compound of claim 2 when $R^3$ is hydrogen and $R^2$ is not hydroxy$(C_1-C_6)$alkoxy.

42. A method of treating memory dysfunction characterized by decreased cholinergic function with 6-O- demethylgalanthamine which comprises administering to a mammal an acetylcholinesterase inhibiting amount of the compound of claim 31 when $R^3$ is hydrogen.

43. The compound of claim 32 which is 6-O-demethyl-6-O-[2-(methyl)butan-2-yloxycarbonyl]galanthamine or a pharmaceutically acceptable acid addition salt thereof.

44. The compound of claim 33 which is 6-O-demethyl-3-O-(t-butoxycarbonyl)-6-O-(t-butylcarbonyl)galanthamine or a pharmaceutically acceptable salt thereof.

45. The compound claim 2 wherein $R^1$ is hydrogen, $(C_1-C_{12})$alkylcarbonyl or $(C_1-C_{12})$alkoxycarbonyl;

$R^2$ is $(C_1-C_6)$alkoxycarbonyl$(C_1-C_6)$alkoxy or hydroxy $(C_1-C_6)$alkoxy; and $R^3$ is hydrogen or bromo.

46. The compound of claim 45 which is 6-O-demethyl-O-6-(ethoxycarbonyl)methylgalanthamine and its pharmaceutically acceptable acid addition salts.

47. The compound of claim 45 which is 6-O-demethyl-6-O-(2-hydroxyethyl)-galathamine and its pharmaceutically acceptable acid addition salts.

48. A pharmaceutical composition which comprises a pharmaceutically acceptable carrier and an acetylcholinesterase inhibiting amount of the compound of claim 1.

49. A method of treating memory dysfunction characterized by decreased cholinergic function which comprises administering to a mammal an acetylcholinesterase inhibiting amount of the compound of claim 1.

* * * * *